United States Patent
Mohajer

Patent Number: 5,464,409
Date of Patent: Nov. 7, 1995

[54] UTERINE MANIPULATOR AND PROTECTOR

[76] Inventor: Reza S. Mohajer, 3115 W. Shore Dr., Orchard Lake, Mich. 48033

[21] Appl. No.: 163,502

[22] Filed: Dec. 9, 1993

[51] Int. Cl.⁶ .......................... A61B 17/00; A61M 29/00
[52] U.S. Cl. .............. 606/119; 604/96; 600/227
[58] Field of Search .................... 128/20, 774, 778; 604/96, 97, 102–109, 55, 164, 264, 329–331; 686/1, 108, 119, 190–193, 198

[56] References Cited

U.S. PATENT DOCUMENTS

| | | | |
|---|---|---|---|
| 2,400,251 | 5/1946 | Nagel | 606/119 |
| 2,480,041 | 8/1949 | Myller | |
| 3,721,229 | 3/1973 | Panzer | |
| 3,833,004 | 9/1974 | Vazquez et al. | |
| 3,877,433 | 4/1975 | Librach | 606/119 |
| 3,882,852 | 5/1975 | Sinnreich | 128/4 |
| 3,896,816 | 7/1975 | Mattler | |
| 3,926,192 | 12/1975 | Van Maren | |
| 3,948,270 | 4/1976 | Hasson | |
| 4,000,743 | 1/1977 | Weaver | |
| 4,089,337 | 5/1978 | Kronner | |
| 4,430,076 | 2/1984 | Harris | 604/96 |
| 4,585,438 | 4/1986 | Makler | 604/106 |
| 4,775,362 | 10/1988 | Kronner | 604/96 |
| 4,976,717 | 12/1990 | Boyle | 606/119 |
| 4,997,419 | 3/1991 | Lakatos et al. | 604/55 |
| 5,037,430 | 8/1991 | Masson | 606/119 |
| 5,104,377 | 4/1992 | Levine | 606/193 |
| 5,209,754 | 5/1993 | Ahluwalia | 606/193 |
| 5,284,162 | 2/1994 | Wilk | 606/205 |

FOREIGN PATENT DOCUMENTS

| 0319394 | 6/1989 | European Pat. Off. | 606/119 |

OTHER PUBLICATIONS

*Journal of Reproductive Medicine*, vol. 38, No. 7; pp. 534–536 (Jul. 1993), F. Nezhat et al; "Adhesion formation After Endoscopic, Posterior Colotomy".

*Obstetrics and Gynecology Forum*, vol. VI, No. 4, pp. 2, 12–14; (May 1993) Dorsey et al; "Laparoscopically Pelvic Reconstruction for Vaginal and Uterine Prolapse and Urinary Stress Incontinenece".

*Obstetrics and Gynecology Forum*, vol. VI, No. 4, pp. 3–5, 9; (May 1993) Dorsey et al. "Laparoscopically Assisted Vaginal Hysterectomy".

*Journal of Reproductive Medicine*, vol. 38, No. 7, pp. 537–542 (Jul. 1993); Daniell et al.; "Laparoscopically Assisted Vaginal Hysterectomy".

Brochure, "ZUMI–4.5 Zinnanti Uterine Manipulator/Injector" (undated); Zinnanti Surgical Instruments, Inc., Chatsworth, Calif. 91311.

Primary Examiner—Stephen C. Pellegrino
Assistant Examiner—Glenn Dawson
Attorney, Agent, or Firm—Gifford, Krass, Groh, Sprinkle, Patmore, Anderson & Citkowski

[57] ABSTRACT

A uterine manipulator and protector. It includes a shield member configured to engage with the area surrounding the external cervical os. The shield member has a curved blade projecting from an edge thereof for extension into the posterior vaginal cul de sac. Also formed on an interior surface of the shield member is a finger which extends into the cervix. An elongated handle terminating in an exovaginal portion graspable by the user extends from the exterior surface of the shield member.

10 Claims, 3 Drawing Sheets

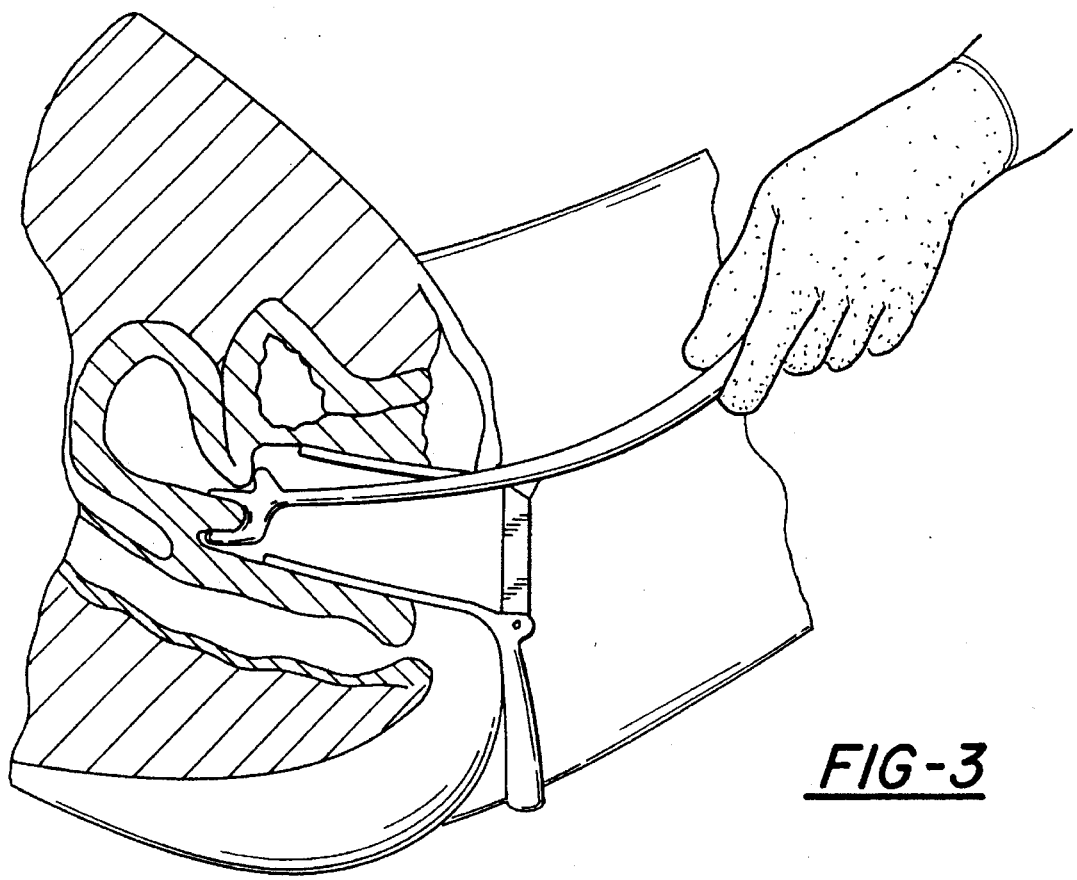
FIG-3
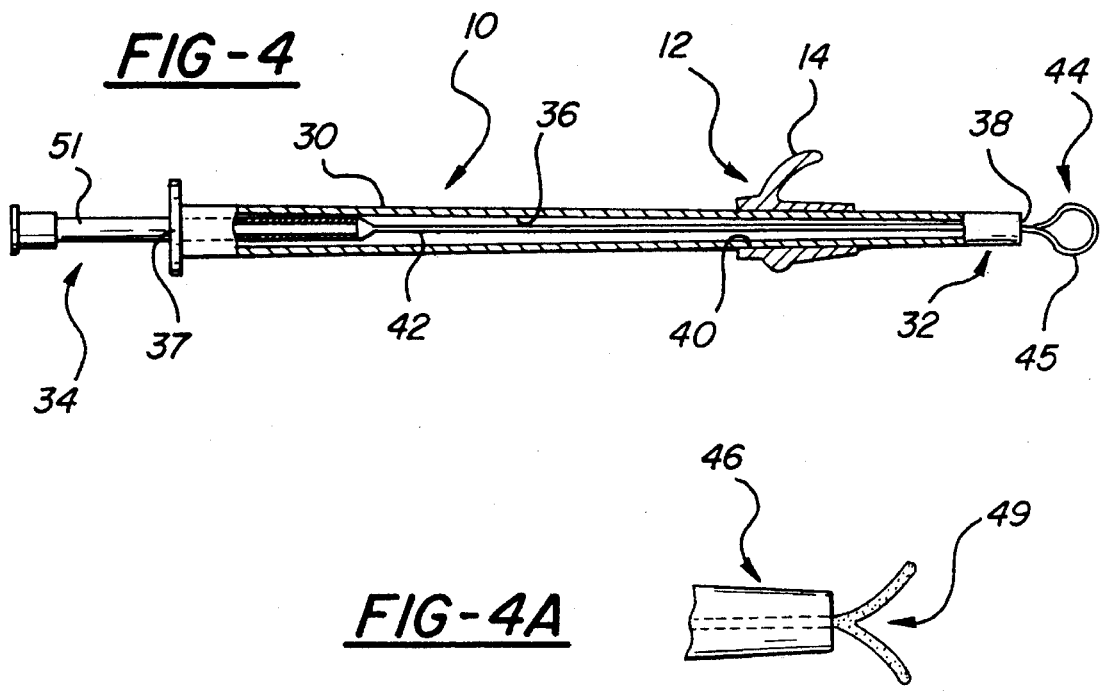
FIG-4
FIG-4A

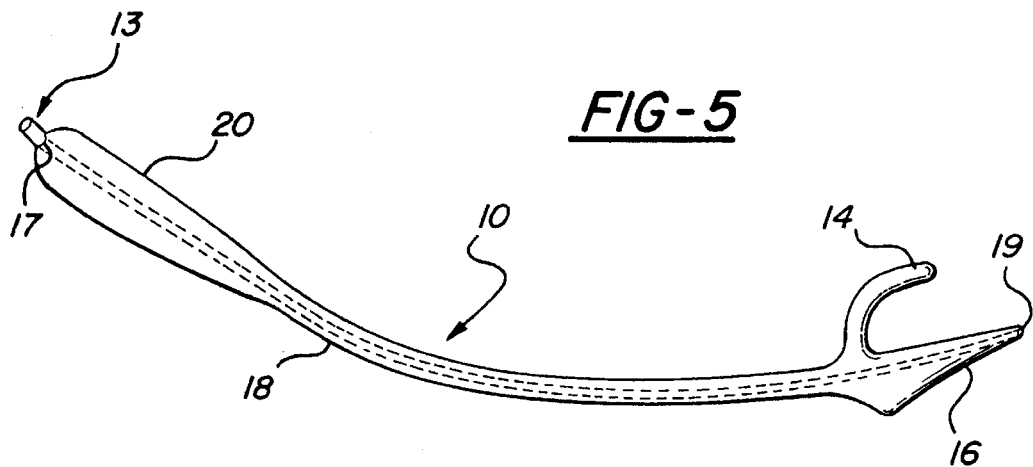
FIG-5
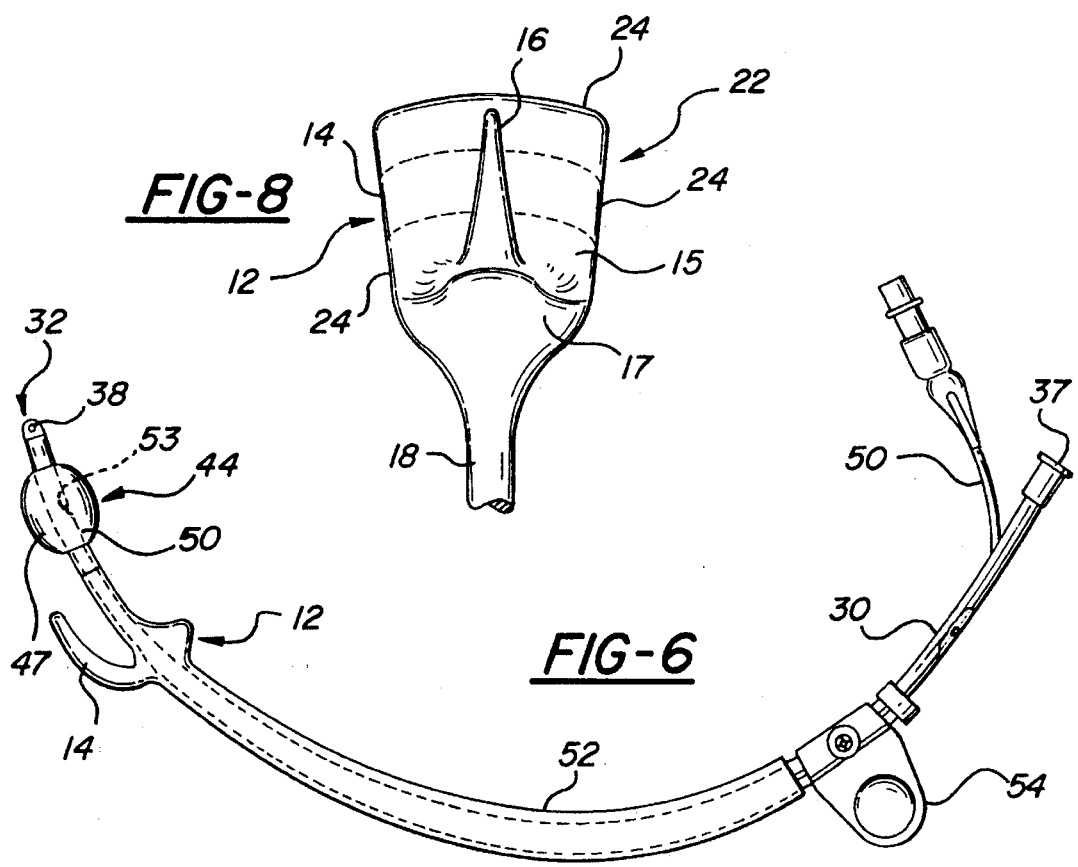
FIG-8
FIG-6
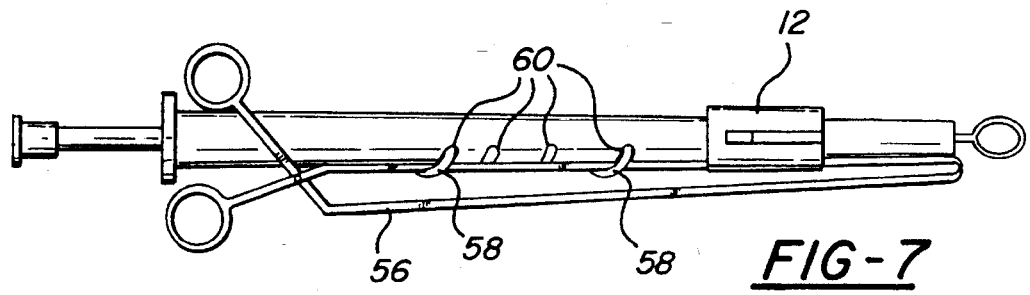
FIG-7

UTERINE MANIPULATOR AND PROTECTOR

BACKGROUND OF THE INVENTION

1. Field of the Invention

The present invention concerns the field of uterine manipulators and, more particularly, to such a manipulator including a multi-functional cup-shaped shield having an open front and which is multifunctional to protect the outer uterine wall from trauma, provide means for manipulating and retracting the uterus in all directions, and also seal the uterine cavity.

2. Description of the Relevant Prior Art

There are a variety of prior art uterine manipulators used in positioning the uterus during various surgical procedures, such as anterior and posteriorial abdominal colpotomy, total laparoscopic hysterectomy, partial laparoscopic hysterectomy, laparoscopy assisted hysterectomy, and laparoscopy assisted vaginal hysterectomy, as well as other procedures and examinations. Generally, during the performance of a laparoscopic procedure, a small incision is made in the wall of the abdomen and a laparoscope is inserted therethrough to permit visualization of the peritoneal cavity and the uterus. Uterine manipulators also frequently function as catheters for irrigating the uterine cavity, particularly during radio imaging procedures such as hysteroselpingraphy.

A number of uterine manipulators and irrigators have been developed to assist the physician in visualizing the uterus and facilitating the performance of these various examinations and procedures. See, for example, U.S. Pat. Nos. 3,926,192; 4,000,743; 4,089,337; 4,430,076; 4,775,362; 4,976,717; 4,997,419; 4,997,419; and 5,209,754. Typical of these are: U.S. Pat. No. 4,000,743, which describes a uterine anteverter which includes an arcuately curved shield which limits the distance a manipulating arm can be extended into the uterine cavity; U.S. Pat. No. 4,775,362, which describes a uterine manipulator including a catheter tube with an insertable end adapted to be inserted into the uterus, an adjustable stop adapted to engage the cervix mounted on and shiftable axially along the catheter tube, and a digitally actuated clamp which is positioned outside the external opening of the vagina with the manipulator in place; and U.S. Pat. No. 5,209,754 which describes a vaginal cervical retractor used to maneuver and visualize the uterus including an inner tube provided with a removable pair of plastic caps designed to be inserted into the uterine cavity and a cervical cap secured to the tube to ensure that the tube does not extend beyond a certain distance into the uterus. Furthermore, a rigid, metal cup shaped catheter tube is also manufactured by the Story Company, a German concern, and marked with the number 26168T.

None of the prior art medical instruments are completely satisfactory. In particular, none of them provide any shielding for the lower segment of the posterior uterine wall which extends into the vaginal posterior cul-de-sac and which, during laparoscopic surgery, is particularly vulnerable to damage from laser beams, as well as conventional surgical trauma. Moreover, it is difficult to identify the positions of the posterior cul-de-sac and the rectum, which lies behind the cul-de-sac during abdominal laparoscopic surgery, and this sometimes results in trauma to the rectum, a highly undesirable outcome. The possibility of injury to the posterior uterine wall and rectum has been noted in the literature. For example, in an article entitled "Adhesion Formation After Endoscopic Posterior Colpotomy", *Journal of Reproductive Medicine*, volume 38, no. 7, pp. 534–536, F. Nezhat et al. note: "Surgical entry into the posterior vagina by colpotomy does enlist the potential for significant complications. Rectal injury may occur when the rectovaginal reflector rests high upon the uterosacral hiatus." Furthermore, the prior art devices tend to be both inefficient at sealing the uterine cavity, and awkward and complicated to use. What is really needed is a simple, well designed instrument which facilitates manipulation of the uterus during surgical procedures, which helps to protect the vaginal posterior cul-de-sac wall from damage, and, optionally, effectively seals the uterine cavity. It would also be highly desirable if such a device could serve as a marker to identify the position of the posterior cul-de-sac and reduce or eliminate trauma to the rectum.

SUMMARY OF THE INVENTION

The present invention is designed to overcome the problems in the prior art noted above. In its broadest aspect, the invention is a combination uterine retractor and shield which includes a shield member having an open front and configured to engage a lower segment of the posterior uterine wall adjacent the external cervical os. The shield member includes a curved blade projecting from an edge thereof and configured to extend into the posterior vaginal cul-de-sac to protect the lower posterior uterine wall and rectum from trauma and a finger projecting from an inner surface of the shield member and extending for a distance into the cervix for engagement therewith. An elongated handle is attached to an outer surface of the shield member and terminates in an exo-vaginal portion which is graspable by a user so that the uterus of a patient undergoing a medical procedure may be manipulated, retracted and protected from trauma during the procedure. Furthermore, the shield serves to mark the position of the cul-de-sac relative to the rectum, thus minimizing the risk of trauma to the rectum from laser, cautery or other instruments. Preferably, the elongated handle is curved so as to conform to the natural curvature of the vaginal canal and cervix, and to fit in the posterior cul-de-sac.

In a particularly preferred embodiment, the shield member further includes means for adjusting the length of the curved blade to accommodate a variety to anatomical variations and different shaped cervixes. Typically, the means for adjusting comprises at least one, and preferably a plurality, of curved extensions attachable to the curved blade so as to lengthen and widen it.

In another aspect of the present invention, the combination uterine retractor and shield also functions to irrigate the uterine cavity. This embodiment includes an elongate tube having an insertable end configured to be inserted through the cervix into the uterine cavity, and an opposite, exo-vaginal end, the tube having means defining a passage extending therealong for the introduction of fluid therethrough, such as a radio opaque fluid or fluid including a radio opaque dye. A shield member having an open front and configured to engage a portion of the outer uterine wall adjacent the external cervical os is slidably positionable on said tube. The shield has means forming a bore extending therethrough for passage of the elongate tube therethrough. The shield member further includes a curved blade projecting from an edge thereof and configured to extend into the posterior vaginal cul-de-sac to protect the posterior uterine wall and rectum from trauma and a finger projecting from an inner surface of the shield member and extending a distance into the cervix for engagement therewith. An elongated, flexible member is disposed in said passageway and has a first end including expansible means for engagement with the uterine cavity and for fixing the position of the shield member relative to the elongate tube so that the shield member may be properly positioned relative to the entrance of the cervix.

Optionally, this embodiment may further include an inlet port adjacent the opposite end of the elongate tube and a discharge port adjacent the insertable end. The expansible means for engagement with the uterine cavity may be the form of an inflatable balloon which is disposed surrounding the discharge port. An air pump or comparable air supply is in fluid communication with the passageway of the elongated tube so that air may be introduced into the balloon after the insertable end of the elongate member has been inserted into the uterus to inflate the balloon and seal the uterine cavity. The balloon, coacting with the shield member which conforms to the shape of the area surrounding the external cervical os, effectively seals the uterine cavity.

In another preferred embodiment, the means for engagement with the uterine cavity may comprise a resilient, multi-armed prong which is biased for movement from a first, retracted position to a second, expanded position, said elongated member serving to hold said prong in said retracted position inside said tube while said insertable end of said tube is being inserted through the cervix into the uterine cavity and to advance the prong through the insertable end of the tube into the uterine cavity when the device is in place. Again, the multi-arm prong cooperates with the shield member so that the uterine wall is securely grasped therebetween to facilitate in manipulating the uterus.

In yet another aspect of the present invention, the improved uterine manipulator device comprises an elongate tube having an insertable end adapted to be inserted through the cervical canal into the uterine cavity and an opposite end which locates outside the external opening of the vagina with the manipulator device in place. The tube includes means defining a passage extending therealong, and the passage has an inlet port adjacent its opposite end and terminates in a discharge port adjacent the insertable end. The passage serves to channel fluid introduced thereinto along the tube to deliver it to the discharge port.

An inflatable member such as a balloon is mounted on the discharge end of the tube with the interior thereof communicating with the discharge port and is adapted to be inflated with the fluid channeled by said passage.

An elongate plastic sheath having an external passage extending therealong is disposed on the tube such that the tube is lodged loosely within the internal passage with the sheath in nonclamping relation relative thereto and freely slidable relative thereto. A shield member having an open or partially open front is integrally formed at one end of the sheath, also in loose slidable relation with respect to the tube and located adjacent but inwardly from the tube's insertable end. The shield member is configured to engage a portion of the outer uterine wall adjacent the external cervical os. The shield member includes a curved blade projecting from an edge thereof and configured to extend into the vaginal cul-de-sac to protect the posterior uterine wall and rectum from trauma, and a finger projecting from an inner surface of the shield member and extending for a distance to the cervical canal for engagement therewith. The device also includes means for fixing the position of the sheath relative to the tube so that the shield may be properly positioned relative to the entrance of the cervix.

The device of the present invention may be molded from a resilient material such as a polymeric resin. Preferably, the shield member of the present invention is formed of a laser opaque material, thus serving to protect the uterine wall and rectum from accidental laser burn or perforation.

Optionally, the uterine manipulator of the present invention may include a tenaculum for grasping a cervix and means for attaching the tenaculum to the elongate handle of the device. An adjustable hook is disposed on the handle of the device; thusly, the tenaculum can be fastened on it during manipulation. The attached tenaculum aids in firmly holding the ,uterus in position while the medical procedure is performed.

BRIEF DESCRIPTION OF THE DRAWINGS

The following detailed description is best understood by reference to the following drawings in which:

FIG. 3 shows the uterine manipulator of FIG. 1 used to depress the uterine fundus;

FIG. 4 shows an alternate embodiment of a uterine manipulator according to the present invention; and FIG. 4a shows an alternate embodiment of the means for engagement thereof;

FIGS. 5 and 6 show other alternate embodiments of a uterine manipulator according to the present invention;

FIG. 7 shows yet another alternate embodiment of the uterine manipulator including a tenaculum attached thereto; and FIG. 8 is a broken away, perspective view of the shield member including a plurality of detachable extensions.

DETAILED DESCRIPTION OF THE PREFERRED EMBODIMENTS

Figure 1:
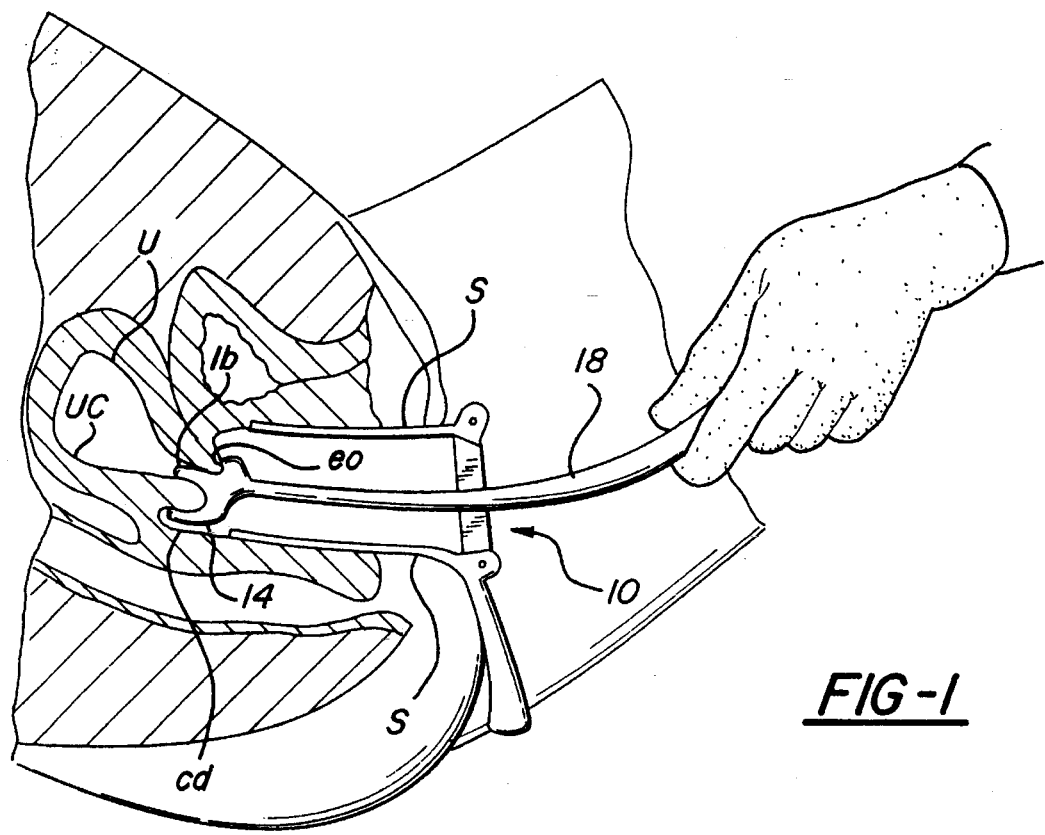
FIG. 1 depicts a uterine manipulator according to the present invention in position during a surgical procedure.

Throughout the following detailed description, like numerals are used to reference the same element of the invention shown in multiple figures thereof. Referring now to the drawings, and in particular FIGS. 1, 5 and 8, there is shown a uterine manipulator 10 according to the present invention. The uterine manipulator 10 includes a shield member 12 which is configured to engage portions of the uterine fundus adjacent the external cervical os (EO). As is best seen in FIG. 8, the shield member 12 includes a curved blade 14 which is formed on an edge thereof and which is configured to extend into the posterior cul-de-sac (CD) in the manner shown in FIG. 1. The shield member 12 also includes a finger 16 projecting from an inner surface 15 thereof for engagement with the cervix. Extending from an outer surface 17 of the shield member 12 is an elongate, hollow handle 18 (preferably curved) which terminates in an exo-vaginal portion 20, best seen in FIG. 5. A fluid inlet part 17 and outlet part 19 open onto, respectively, on exo- and endo-cervical ends 13, 15 of the device 10.

Figure 2:
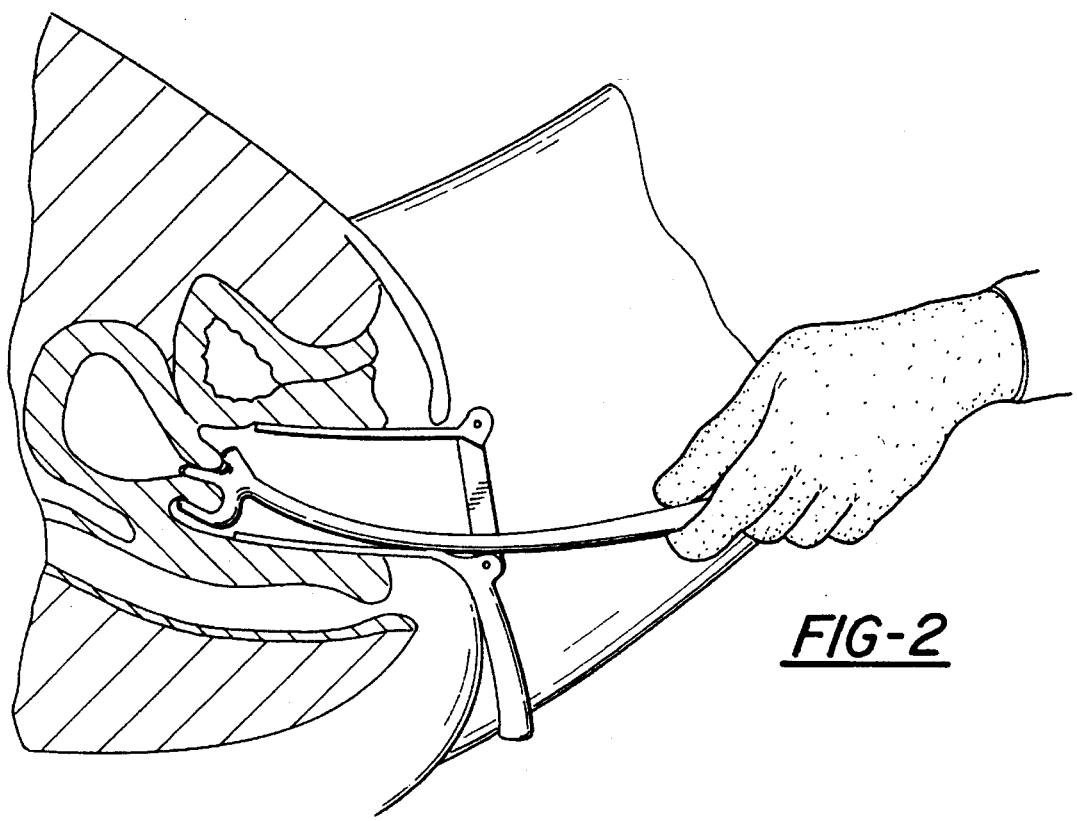
FIG. 2 shows the uterine manipulator of FIG. 2 used to elevate the uterine fundus.

The manner of use of the uterine manipulator 10 is shown in FIGS. 1, 2 and 3. In FIG. 1, the vaginal canal has been dilated by means of a speculum, the blades of which are referenced by S. The device 10 has been passed through the vaginal canal so enlarged and positioned so that the cup shaped shield member 14 is in registry with the outer uterine wall and the finger 16 extends into a portion of the cervix via the external os EO of the cervix. The blade 14 then projects into the posterior cul-de-sac CD, thus serving both to protect portions of the uterine wall, and to aid in positioning the uterus during a medical procedure.

In FIG. 2, the exo-vaginal portion 20 of the device 10 has been depressed, thus causing the shield member 14 to pivot upwardly and raise the lobes of the uterine fundus. This movement enlarges the size of the posterior cul-de-sac CD so that the posterior wall thereof is exposed for incision, etc., such as may be useful when performing posterior colpotomy from an abdominal approach. In contrast, FIG. 3 shows the handle of the device lifted, thus causing the shield member 14 to pivot downwardly, and enlarge the anterior vaginal cul-de-sac. Such a maneuver finds usefulness in other types of surgical procedures. Thus, by manipulating the handle 18 of the device 10, the uterus may be easily and securely positioned as desired during a particular medical procedure. Additionally, the engagement of the shield member 14 with the area surrounding the external cervical os, as well as the extension of the finger 18 into the cervix serves to help seal the uterine cavity if desired.

The shield member 12 depicted in FIG. 8 includes means for adjustment 22 in the form of a plurality of extensions 24 which attach to the curved blade 14, thus serving to extend and enlarge it. This adjustability is useful for accommodating a variety of patients having different anatomical dimensions.

Since it is often necessary to both manipulate the uterus and irrigate the uterine cavity during the same medical procedure, this capability has been provided for the embodiments of the present invention shown in FIGS. 4, 6 and 7. In the embodiments shown in FIG. 4, the shield member 12 is positionable upon the length of an elongate tube 30 having a first end 32 and a second end 34. The elongated tube 30 further includes means forming a passageway 36 therethrough which terminates in inlet port 37 disposed proximate second end 34 and discharge port 38 disposed proximate first end 32. In this case, the shield member 12 has a bore 40 formed therethrough so that shield member 12 may be slidingly moved along the length of elongate tube 32. Means such as molded-in stops (not shown) may be formed on the outer surface of elongate tube 30 to provide a means for adjusting the position of shield member 12.

An elongate, resilient member 42, such as a strand of metallic or polymeric material having sufficient stiffness to function as described, is disposed inside passageway 36. Disposed on a free end 44 of resilient member 42 is expansible means 46 for engaging the uterine cavity to hold the first end 32 of the uterine manipulator 10 in place even when manipulations are performed. The expansible means 46 may comprise a resilient loop 45, balloon 47 (shown in FIG. 6), or a multi-armed prong 49, shown in FIG. 4a. Multi-armed prong 49 is also formed of a resilient material so that it will expand from a compressed position when it is inside the passageway 36 of elongate tube 30 to the expanded configuration (shown in FIG. 4a) when it is pushed through the discharge port 38 of elongate tube 30. For that purpose, a plunger 51 is disposed for sliding movement with respect to elongate tube 30 in the manner depicted in FIG. 4, which shows the device in the extended position. Retraction of the plunger 51 will cause expansible means 46 to retract back into elongate tube 30.

In the embodiment depicted in FIG. 6, an air line 50 is provided to introduce air into balloon 47 so that it expands after the first end 32 of the device 10 has been introduced into the uterine cavity, thus serving to help seal off the uterine cavity to prevent discharge of fluid therefrom. In this embodiment, the discharge port 38 is disposed outboard of the balloon 44 and an air discharge port 53 is located inside the balloon 44.

In the embodiment shown in FIG. 6, the shield number 12 is disposed on a sheath 52 which surrounds elongate tube 30. Thus, both sheath 52 and shield member 12 are disposed in sliding relationship with respect to elongate tube 30. Clamp 54 provides means for fixing the position of sheath 52 and shield member 12 with respect to tube 30. Thus, the distance between shield member 12 and balloon 44 may be adjusted. Elongate tube 30 may include indicia formed thereon (not shown) indicating length gradations. The device 10 may be inserted into the patient and a preliminary measurement made prior to actually fixing the position of shield member 12.

Since it is frequently necessary to employ a tenaculum in conjunction with uterine manipulation, the embodiment of the present invention shown in FIG. 7 includes a tenaculum 56 mounted on elongate tube 30. In other respects, the embodiment of FIG. 7 is similar to that shown in FIG. 4 and will not otherwise be described in detail. Means in the form of hooks 58 are provided for attaching the tenaculum 56 to the device 10. The hooks 58 are insertable into a plurality of apertures 60 formed in the handle 18 of the device. The open front of the shield member 12 facilitates the positioning of the tenaculum 56.

Thus, there has been described a uterine manipulator and protector which is easy to manufacture (some embodiments may be molded from a single piece of plastic), easy to use, provides a secure grip on the uterus for manipulation, and also helps to protect portions of the uterine wall. The device may include further elements which allow it to simultaneously serve as a uterine catheter. The device of the present invention has been depicted with regard to certain embodiments and exemplifications. Doubtless, by utilizing the teachings of the present disclosure, certain design variations may be obvious to one skilled in the art without departing from the spirit of the present invention. It is the claims appended hereto and all reasonable equivalents thereof, rather than the depicted embodiments and exemplifications, which define the true scope of the present invention.

I claim:

1. A combination uterine retractor and shield device comprising:

an elongated tube having an insertable end configured to be inserted through the cervical canal into the uterine cavity, and an opposite, exo-vaginal end said tube having means defining a passage extending therealong;

a shield member having an at least partially open face and configured to engage a portion of the outer uterine wall adjacent the external cervical os and having means forming a bore extending therethrough for passage of said elongate tube therethrough such that said shield member is slidably positionable on said tube, said shield including:

a curved blade projecting from a portion of an edge of said shield member and configured to extend into the posterior vaginal cul-de-sac to protect the posterior uterine wall from trauma; and a finger projecting from an inner surface of said shield member and configured to extend for a distance into the cervix for engagement therewith;

an elongated, flexible member disposed in said passage and having a first end including expansible means for engagement with the uterine cavity formed thereon; and means for fixing the position of the shield member with respect to the tube such that the device may be positioned with the means for engagement inside of the uterine cavity and the shield in registry with said portion of the outer uterine wall, the means for engagement being expandable to engage an inner surface of the uterus and clamp the uterine wall between the means for engagement and the shield member such that the posterior uterine wall may be manipulated, retracted and protected from trauma during a medical procedure.

2. The device of claim 1 wherein the passage further comprises an inlet port adjacent the exo-vaginal end and a discharge port adjacent said insertable end, said passage serving to channel fluid introduced thereinto along the tube for discharge into the uterus, egress of said fluid from the uterus being prevented by said shield member.

3. The device of claim 1 wherein the expansible means for engagement with the uterine cavity comprises a resilient, multi-armed prong which is biased for movement from a first, retracted position to a second, expanded position, said resilient, elongated member serving to hold said prong in said retracted position inside said tube while said insertable end of said tube is being inserted through the cervix into the uterine cavity and to advance said prong through the insertable end of said tube and into the uterine cavity to assume said expanded position.

4. The device of claim 1 wherein said means for engagement with the uterine cavity comprises a resilient loop.

5. The device of claim 1 wherein the shield member further includes means for adjusting the size of the curved blade to accommodate anatomical variations.

6. The device of claim 5 wherein the means for adjusting comprises at least one extension attachable to said curved blade.

7. The device of claim 1 wherein the shield member is formed of a laser reflective material.

8. An improved uterine manipulator device comprising:

an elongated tube having an insertable end adapted to be inserted through the cervical canal into the uterine cavity and an opposite end configured to be located outside the external opening of the vagina with the manipulator device in place, said tube having means defining a passage extending therealong and the passage having an inlet portion adjacent its said opposite end and terminating in a fluid discharge port adjacent said insertable end, said passage serving to channel fluid introduced thereinto along the tube with such fluid delivered to said discharge port;

an air line disposed inside said passage and terminating in an air discharge port spaced from said fluid discharge port;

an inflatable member affixed to said tube proximate said insertable end of the tube and including an interior communicating with said air discharge port and adapted to be inflated with air channeled by said air line;

an elongate plastic sheath having an internal passage extending therealong, said tube being lodged loosely within said internal passage with the sheath in non-clamping relation relative thereto and thus freely slidable relative to the tube;

a shield member having an at least partially open face and integrally formed on one end of the sheath, also in loose slidable relation with respect to the tube, located adjacent but proximally of the tube's insertable end, said shield configured to engage a portion of the outer uterine wall adjacent the external cervical os, said shield including:

a curved blade projecting from a portion of an edge of said shield member and configured to extend into the vaginal cul-de-sac to protect the posterior uterine wall from trauma; and a finger projecting from an inner surface of said shield member and adapted to extend for a distance into the cervix for engagement therewith; and means for fixing the position of the sheath relative to the tube so that the shield member may be properly positioned relative to the external cervical os.

9. The device of claim 8 wherein the shield member further includes means for adjusting the size of the curved blade to accommodate anatomical variations.

10. The device of claim 9 wherein the means for adjusting comprises at least one extension attachable to said curved blade.

* * * * *